(12) United States Patent
Adams (10) Patent No.: US 8,172,801 B2
(45) Date of Patent: May 8, 2012

(54) METHOD FOR POSITIONING A CATHETER GUIDE ELEMENT IN A PATIENT AND KIT FOR USE IN SAID METHOD

(75) Inventor: Mark L. Adams, Sandy, UT (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 916 days.

(21) Appl. No.: 11/228,614

(22) Filed: Sep. 15, 2005

(65) Prior Publication Data

US 2007/0078430 A1  Apr. 5, 2007

(51) Int. Cl.
*B65D 69/00* (2006.01)
*A61B 1/00* (2006.01)
*A61B 1/01* (2006.01)
*A61B 17/10* (2006.01)
*A61B 17/04* (2006.01)
*A61M 25/00* (2006.01)
*A61M 5/178* (2006.01)

(52) U.S. Cl. .......... 604/164.01; 206/570; 600/101; 600/104; 600/585; 604/164.12; 604/166.01; 604/170.02; 606/139; 606/148

(58) Field of Classification Search .......... 600/585, 600/101, 104; 604/164.01, 164.12, 166.01, 604/170.02; 206/570; 606/139, 148
See application file for complete search history.

(56) References Cited

U.S. PATENT DOCUMENTS

| 2,472,527 | A | * | 6/1949 | Gordon et al. | 403/212 |
| 3,508,545 | A | * | 4/1970 | Prather et al. | 604/158 |
| 3,539,034 | A | * | 11/1970 | Tafeen | 604/164.09 |
| 3,701,367 | A | * | 10/1972 | Ackerman | 140/119 |
| 3,877,434 | A | * | 4/1975 | Ferguson et al. | 606/158 |
| 3,929,123 | A | * | 12/1975 | Jamshidi | 600/567 |
| 3,995,619 | A | * | 12/1976 | Glatzer | 600/550 |
| 4,573,576 | A | * | 3/1986 | Krol | 206/471 |
| 4,758,219 | A | * | 7/1988 | Sacks et al. | 604/506 |

(Continued)

FOREIGN PATENT DOCUMENTS

JP  08215200 A * 8/1996

(Continued)

*Primary Examiner* — Sean Dougherty
(74) *Attorney, Agent, or Firm* — Kenyon & Kenyon LLP (57) ABSTRACT

A method for positioning a guide element in a patient and a kit for use in the method. In one embodiment, the method involves transorally inserting an endoscope into a patient's stomach. An incision site is externally indicated by transilluminating the stomach and abdominal walls of the patient from within the stomach. Next, a scalpel incision is made at the indicated incision site, and an access needle is inserted into the incision, the proximal end of the access needle remaining external to the patient and the distal end of the access needle extending into the patient's stomach. The stylet of the access needle is then removed from the patient while keeping the cannula in place. Next, the distal end of a grasping tool is inserted through the cannula and into the patient's stomach. The looped leading end of a pullwire is then inserted through the endoscope and into the stomach. The tool is then manipulated until a distal hook on the tool catches the looped leading end. Next, the tool and the looped leading end are withdrawn from the patient through the cannula. The endoscope is then withdrawn from the patient over the trailing end of the pullwire. In this manner, the pullwire is positioned so that the trailing end of the pullwire extends from the patient's mouth and the leading end of the pullwire extends from the incision.

22 Claims, 9 Drawing Sheets

U.S. PATENT DOCUMENTS

| | | | |
|---|---|---|---|
| 4,826,481 A * | 5/1989 | Sacks et al. | 604/516 |
| 4,861,334 A | 8/1989 | Nawaz | |
| 4,900,306 A | 2/1990 | Quinn et al. | |
| 5,015,250 A * | 5/1991 | Foster | 606/147 |
| 5,059,201 A * | 10/1991 | Asnis | 606/144 |
| 5,100,404 A * | 3/1992 | Hayes | 606/62 |
| 5,100,418 A * | 3/1992 | Yoon et al. | 606/139 |
| 5,112,310 A | 5/1992 | Grobe | |
| 5,167,627 A * | 12/1992 | Clegg et al. | 604/103.03 |
| 5,181,919 A * | 1/1993 | Bergman et al. | 606/144 |
| 5,197,484 A * | 3/1993 | Kornberg et al. | 600/567 |
| 5,250,054 A * | 10/1993 | Li | 606/148 |
| 5,259,399 A * | 11/1993 | Brown | 128/897 |
| 5,318,543 A * | 6/1994 | Ross et al. | 604/170.01 |
| 5,320,110 A * | 6/1994 | Wang | 600/566 |
| 5,330,488 A * | 7/1994 | Goldrath | 606/148 |
| 5,356,382 A * | 10/1994 | Picha et al. | 604/105 |
| 5,364,410 A * | 11/1994 | Failla et al. | 606/148 |
| 5,383,466 A * | 1/1995 | Partika | 600/459 |
| 5,391,159 A | 2/1995 | Hirsch et al. | |
| 5,392,766 A * | 2/1995 | Masterson et al. | 600/157 |
| 5,405,354 A * | 4/1995 | Sarrett | 606/148 |
| 5,445,167 A * | 8/1995 | Yoon et al. | 128/898 |
| 5,454,790 A * | 10/1995 | Dubrul | 604/104 |
| 5,507,279 A * | 4/1996 | Fortune et al. | 128/200.26 |
| 5,540,704 A * | 7/1996 | Gordon et al. | 606/144 |
| 5,573,542 A * | 11/1996 | Stevens | 606/144 |
| 5,643,288 A * | 7/1997 | Thompson | 606/139 |
| 5,647,874 A * | 7/1997 | Hayhurst | 606/232 |
| 5,658,299 A * | 8/1997 | Hart | 606/139 |
| 5,746,753 A * | 5/1998 | Sullivan et al. | 606/147 |
| 5,827,227 A * | 10/1998 | DeLago | 604/104 |
| 5,910,148 A * | 6/1999 | Reimels et al. | 606/144 |
| 5,925,059 A * | 7/1999 | Palermo et al. | 606/191 |
| 6,022,360 A * | 2/2000 | Reimels et al. | 606/144 |
| 6,042,583 A * | 3/2000 | Thompson et al. | 606/232 |
| 6,102,920 A * | 8/2000 | Sullivan et al. | 606/147 |
| 6,346,074 B1 * | 2/2002 | Roth | 600/121 |
| 6,676,673 B2 * | 1/2004 | Chang | 606/144 |
| 6,685,713 B1 * | 2/2004 | Ahmed | 606/140 |
| 6,770,084 B1 * | 8/2004 | Bain et al. | 606/144 |
| 6,918,871 B2 * | 7/2005 | Schulze | 600/114 |
| 7,097,635 B2 * | 8/2006 | McGuckin et al. | 604/164.09 |
| 7,731,696 B2 * | 6/2010 | Hanagasaki | 604/171 |
| 7,753,928 B2 * | 7/2010 | de la Torre et al. | 606/191 |
| 7,794,385 B2 * | 9/2010 | Rosenblatt | 600/30 |
| 7,815,654 B2 * | 10/2010 | Chu | 606/144 |
| 2001/0053916 A1 * | 12/2001 | Rioux | 606/139 |
| 2002/0049449 A1 | 4/2002 | Bhatnagar et al. | 606/94 |
| 2002/0100485 A1 * | 8/2002 | Stevens et al. | 128/898 |
| 2002/0147456 A1 * | 10/2002 | Diduch et al. | 606/144 |
| 2003/0093090 A1 * | 5/2003 | McGuckin et al. | 606/138 |
| 2003/0159966 A1 * | 8/2003 | McMichael et al. | 206/570 |
| 2003/0159967 A1 * | 8/2003 | McMichael et al. | 206/570 |
| 2003/0163143 A1 * | 8/2003 | Wakabayashi | 606/148 |
| 2003/0171642 A1 * | 9/2003 | Schock et al. | 600/18 |
| 2003/0171718 A1 * | 9/2003 | DeLegge et al. | 604/164.01 |
| 2003/0229334 A1 * | 12/2003 | Suzuki | 604/516 |
| 2004/0010273 A1 * | 1/2004 | Diduch et al. | 606/144 |
| 2004/0138531 A1 * | 7/2004 | Bonner et al. | 600/156 |
| 2004/0186487 A1 * | 9/2004 | Klein et al. | 606/148 |
| 2004/0243135 A1 * | 12/2004 | Koseki | 606/80 |
| 2005/0027256 A1 * | 2/2005 | Barker et al. | 604/164.12 |
| 2005/0113848 A1 * | 5/2005 | Reinitz | 606/144 |
| 2005/0154319 A1 * | 7/2005 | Cline et al. | 600/478 |
| 2005/0267415 A1 * | 12/2005 | Jacques | 604/175 |
| 2005/0273129 A1 * | 12/2005 | Michels et al. | 606/185 |
| 2005/0288652 A1 * | 12/2005 | Suzuki | 604/516 |
| 2006/0122458 A1 * | 6/2006 | Bleich | 600/101 |
| 2006/0217589 A1 * | 9/2006 | Wan et al. | 600/29 |
| 2007/0016172 A1 * | 1/2007 | Charukhchian | 606/1 |
| 2007/0106217 A1 * | 5/2007 | DeLegge et al. | 604/104 |
| 2008/0228104 A1 * | 9/2008 | Uber et al. | 600/567 |
| 2010/0016784 A1 * | 1/2010 | Mody et al. | 604/22 |
| 2010/0030019 A1 * | 2/2010 | Kuroda et al. | 600/106 |
| 2010/0198156 A1 * | 8/2010 | Rosch | 604/147 |
| 2010/0219323 A1 * | 9/2010 | Ernst et al. | 248/475.1 |

FOREIGN PATENT DOCUMENTS

| | | | |
|---|---|---|---|
| JP | 2004321725 A | * | 11/2004 |
| JP | 2007054168 A | * | 3/2007 |

* cited by examiner

METHOD FOR POSITIONING A CATHETER GUIDE ELEMENT IN A PATIENT AND KIT FOR USE IN SAID METHOD

BACKGROUND OF THE INVENTION

The present invention relates generally to medical catheters and relates more particularly to guide elements used to implant a medical catheter, such as gastrostomy feeding tube, in a patient.

Certain patients are unable to take food and/or medications transorally due to an inability to swallow. Such an inability to swallow may be due to a variety of reasons, such as esophageal cancer, neurological impairment and the like. Although the intravenous administration of food and/or medications to such patients may be a viable short-term approach, it is not well-suited for the long-term. Accordingly, the most common approach to the long-term feeding of such patients involves gastrostomy, i.e., the creation of a feeding tract or stoma between the stomach and the upper abdominal wall. (A less common approach involves jejunostomy, i.e., the creating of a feeding tract or stoma leading into the patient's jejunum.) Feeding is then typically performed by administering food through a catheter or feeding tube that has been inserted into the feeding tract, with one end of the feeding tube extending into the stomach and being retained therein by an internal anchor or bolster and the other end of the feeding tube extending through the abdominal wall and terminating outside of the patient.

Although gastrostomies were first performed surgically, most gastrostomies are now performed using percutaneous endoscopy and result in the implantation of a feeding tube/internal bolster assembly (also commonly referred to as a percutaneous endoscopic gastrostomy (PEG) device) in the patient. Two of the more common techniques for implanting a PEG device in a patient are "the push method" (also known as "the Sacks-Vine method") and "the pull method" (also known as "the Gauderer-Ponsky method"). Information regarding the foregoing two methods may be found in the following patents, all of which are incorporated herein by reference: U.S. Pat. No. 5,391,159, inventors Hirsch et al., which issued Feb. 21, 1995; U.S. Pat. No. 5,167,627, inventors Clegg et al., which issued Dec. 1, 1992; U.S. Pat. No. 5,112,310, inventor Grobe, which issued May 12, 1992; U.S. Pat. No. 4,900,306, inventors Quinn et al., which issued Feb. 13, 1990; and U.S. Pat. No. 4,861,334, inventor Nawaz, which issued Aug. 29, 1989.

According to the push method, one end of an endoscope is intubated (i.e., inserted) into a patient's mouth and is passed through the esophagus into the stomach. After distension of the stomach by inflation, an entry site on the abdomen is identified using the endoscope for transillumination, and an incision is made by passing the tip of a needle coupled to an outer cannula through the abdominal and stomach walls and into the stomach. One end of the outer cannula remains outside of the body and acts as a stop to limit insertion of the needle and outer cannula into the stomach. A snare is inserted into the stomach via the endoscope and is looped over the inserted end of the needle. The snare is then "walked" up the needle until the outer cannula is snared. The snared cannula is then pulled externally to tack the cannula to the stomach and, in turn, to secure the stomach wall to the abdominal wall. The needle is then removed from the patient while keeping the cannula in place. A first end of a flexible guidewire (also known in the art as a "pushwire") is then passed through the cannula and into the stomach where it is grasped by the snare, the second end of the guidewire remaining external to the patient. The endoscope and the snare are then withdrawn from the mouth of the patient to deliver the first end of the guidewire.

A push-type catheter implanting assembly is then inserted over the first end of the guidewire and is pushed over the guidewire towards its second end. The push-type catheter implanting assembly typically comprises a gastrostomy feeding tube, the gastrostomy feeding tube having a dome-shaped internal bolster disposed at its trailing end and having a tubular dilator serially connected to its leading end. The gastrostomy feeding tube and the internal bolster are typically made of a soft, biocompatible material, like silicone rubber, and may form a unitary structure. The dilator, which tapers in outer diameter from its trailing end to its leading end, is typically made of polyethylene or a like material which is stiffer than silicone but which still possesses some flexibility. Advancement of the push-type catheter implanting assembly over the guidewire continues until the front end of the dilator reaches the cannula and pushes the cannula out through the abdominal wall of the patient. The front end of the dilator is then pulled through the abdominal wall until the front end of the gastrostomy feeding tube emerges from the abdomen and, thereafter, the internal bolster at the rear end of the gastrostomy feeding tube engages the stomach wall. The guidewire is then removed from the patient. The clinician then re-intubates the patient with the endoscope and uses an optical channel in the endoscope to inspect whether the internal bolster is properly seated in the stomach.

If the internal bolster is properly placed against the stomach wall, a length of the externally-extending portion of the implanted gastrostomy feeding tube is then typically cut and removed from the implanted tube to reduce the externally-extending portion of the tube to a desired length (typically about 4-6 inches). (The removal of the leading end of the gastrostomy feeding tube also results in the removal of the dilator, which is connected thereto.) An external bolster is typically secured to the remaining externally-extending portion of the feeding tube to engage the abdomen in such a way as to prevent longitudinal movement of the feeding tube into the stomach. Additionally, a "Y-port" adapter is typically attached to the external end of the feeding tube, the Y-port adapter being adapted to receive a pair of connector tips through which food and/or medications may be dispensed. In addition, a detachable locking clip is typically secured to the implanted feeding tube at a point between the external bolster and the Y-port adapter to prevent gastric fluids from escaping through the proximal end of the feeding tube when the feeding tube is not in use.

The pull method is similar in some respects to the above-described push method, the pull method differing from the push method in that, after the cannula is snared and the needle is removed therefrom, a looped first end of a suture (also known in the art as a "pullwire") is inserted through the cannula and into the stomach where it is grasped by the snare, the second end of the suture remaining external to the patient. The endoscope and the snare are then withdrawn from the mouth of the patient to deliver the first end of the suture. The first end of the suture is then coupled to the leading end of a pull-type catheter implanting assembly, the pull-type catheter implanting assembly typically comprising a gastrostomy feeding tube having an internal bolster at its trailing end and a plastic fitting at its leading end. The plastic fitting typically has a barbed rear portion mounted within the leading end of the feeding tube and a conical front portion that serves as a dilator, said conical front portion tapering in diameter from the leading end of the feeding tube to a front tip. A wire loop is fixed to the front tip of the plastic fitting, the first end of the suture being tied to the wire loop. Using the second end of the suture, the pull-type catheter implanting assembly is then pulled retrograde through the patient until the gastrostomy feeding tube emerges from the abdomen of the patient and the internal bolster engages the stomach wall of the patient. Next, as is the case in the push method, the clinician then re-intubates the patient with the endoscope in order to visually inspect the placement of the internal bolster within the stomach. If the bolster is properly seated in the stomach, the externally-extending portion of the implanted gastrostomy feeding tube is then typically cut to a desired length and one or more of an external bolster, a Y-port and a clamp are attached to the feeding tube.

SUMMARY OF THE INVENTION

It is an object of the present invention to provide a novel method for positioning a guide element (e.g., a pullwire, a pushwire) in a patient.

Therefore, according to one aspect of the present invention, there is provided a method for positioning a guide element in a patient, said method comprising the steps of (a) providing a guide element, said guide element being an elongated member having a leading end and a trailing end; (b) creating an access port in the patient; (c) transorally introducing the leading end of said guide element into the patient, the trailing end of said guide element not being introduced into the patient; and (d) drawing the leading end of said guide element from the patient through said access port, the trailing end of said guide element not being drawn into the patient.

In a preferred embodiment, an endoscope is transorally inserted into a patient's stomach. An incision site is externally indicated by transilluminating the stomach and abdominal walls of the patient from within the stomach. Next, a scalpel incision is made at the indicated incision site, and an access needle is inserted into the incision, the proximal end of the access needle remaining external to the patient and the distal end of the access needle extending into the patient's stomach. The stylet of the access needle is then removed from the patient while keeping the cannula in place. Next, the distal end of a grasping tool is inserted through the cannula and into the patient's stomach. The looped leading end of a pullwire is then inserted through the endoscope and into the stomach. The tool is then manipulated until the tool catches the looped leading end. Next, the tool and the looped leading end are withdrawn from the patient through the cannula. The endoscope is then withdrawn from the patient over the trailing end of the pullwire. In this manner, the pullwire is positioned so that the trailing end of the pullwire extends from the patient's mouth and the leading end of the pullwire extends from the incision.

It should be appreciated that the present method may alternatively be used to position a pushwire, instead of a pullwire.

A pullwire or pushwire, thus positioned in a patient, may then be used to implant a catheter, such as a PEG device, in the patient. For example, where a pushwire has been positioned in the patient, a push-type catheter implanting assembly may be inserted over the trailing end of the guidewire and pushed until an internal bolster at the trailing end of the assembly engages the stomach wall of the patient. Alternatively, where a pullwire has been positioned in the patient, a pull-type catheter implanting assembly may be coupled to the trailing end of the pullwire and then pulled using the pullwire until an internal bolster at the trailing end of the assembly engages the stomach wall of the patient.

The present invention is also directed at a kit for use in positioning a guide element in a patient. According to one embodiment, said kit comprises (a) an access needle, said access needle comprising a cannula and a stylet, said stylet being removably receivable in said cannula; and (b) a guide element grasping tool, said guide element grasping tool comprising a shaft having a proximal end and a distal end, said distal end being insertable through said cannula and having means for grasping a guide element. Said grasping means may be, for example, a hook, a bifurcated structure, an arrowhead or a barbed structure.

According to another embodiment, said kit comprises (a) a device comprising an elongated shaft having a proximal end and a distal end, said distal end being shaped to define a hook adapted to grasp a guide element, said hook having a bend shaped to define a sharp tip; and (b) a cannula, said cannula being sized to permit the distal end of said elongated shaft to be inserted therethrough.

The present invention is further directed at a device for use in positioning a guide element in a patient, said device comprising an elongated shaft having a proximal end and a distal end, said distal end being shaped to define a hook adapted to grasp a guide element, said hook having a bend shaped to define a sharp tip.

For purposes of the present specification and claims, various relational terms like "top," "bottom," "proximal" and "distal" are used to describe the present invention when said invention is positioned in or viewed from a given orientation. It is to be understood that, by altering the orientation of the invention, certain relational terms may need to be adjusted accordingly.

Additional objects, as well as features and advantages, of the present invention will be set forth in part in the description which follows, and in part will be obvious from the description or may be learned by practice of the invention. In the description, reference is made to the accompanying drawings which form a part thereof and in which is shown by way of illustration certain embodiments for practicing the invention. The embodiments will be described in sufficient detail to enable those skilled in the art to practice the invention, and it is to be understood that other embodiments may be utilized and that structural changes may be made without departing from the scope of the invention. The following detailed description is, therefore, not to be taken in a limiting sense, and the scope of the present invention is best defined by the appended claims.

BRIEF DESCRIPTION OF THE DRAWINGS

The accompanying drawings, which are hereby incorporated into and constitute a part of this specification, illustrate various embodiments of the invention and, together with the description, serve to explain the principles of the invention. In the drawings wherein like reference numerals represent like parts.

DETAILED DESCRIPTION OF PREFERRED EMBODIMENTS

Figure 1:
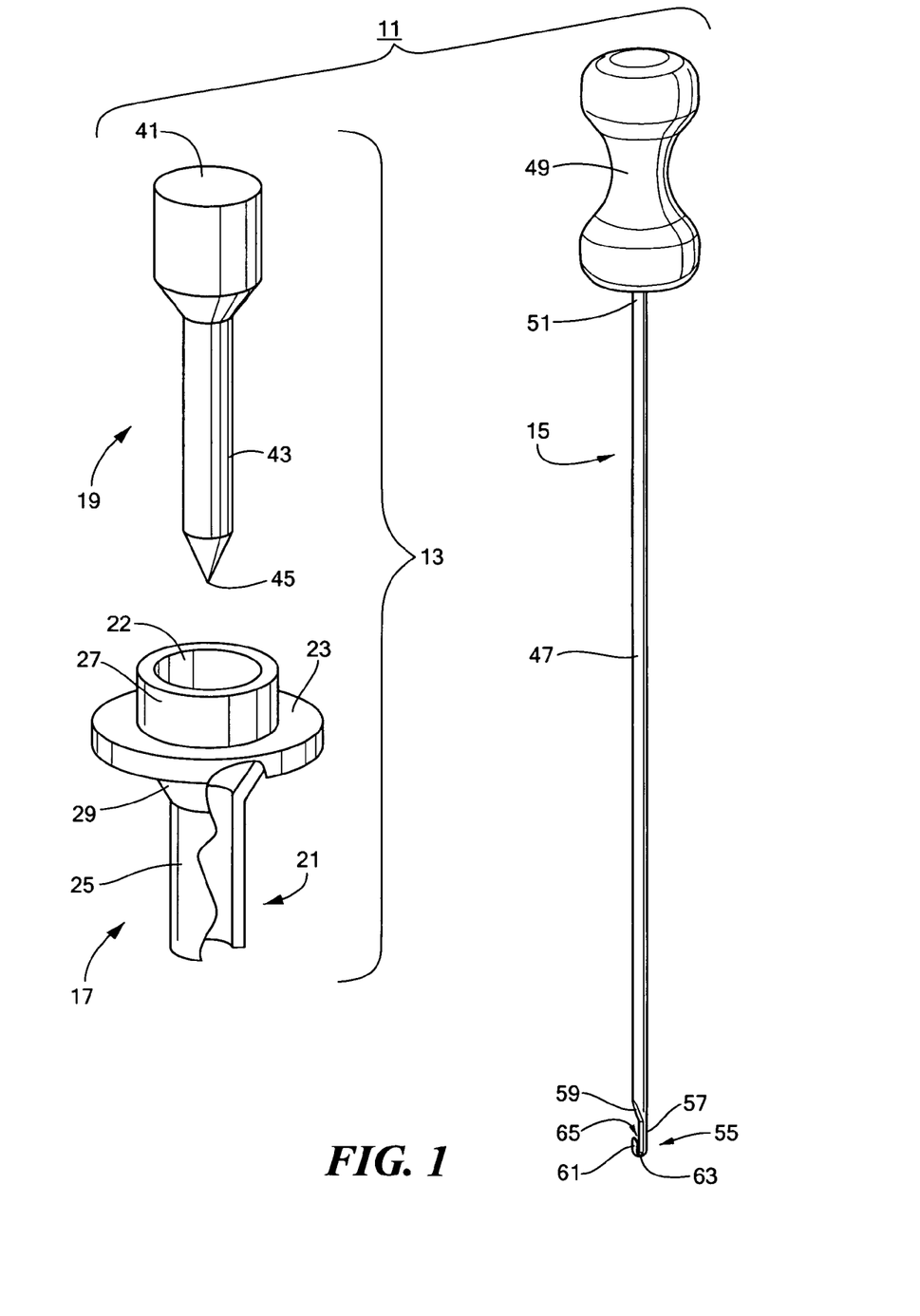
FIG. 1 is an exploded, perspective view of a first embodiment of a kit suitable for use in positioning a guide element in a patient, said kit being constructed according to the teachings of the present invention, the cannula of the access needle being shown broken away in part.

Referring now to FIG. 1, there is shown an exploded perspective view of a first embodiment of a kit constructed according to the teachings of the present invention, said kit being represented generally by reference numeral 11. As will be described below in further detail, kit 11 is adapted for use in positioning a guide element, such as a guidewire (i.e., pushwire) or a suture (i.e., pullwire), in a patient. A guide element, thus positioned, may be used to implant a medical catheter, such as a percutaneous endoscopic gastrostomy (PEG) tube, in the patient's body.

Kit 11 includes an access needle 13 and a guide element grasping tool 15.

Access needle 13 includes a cannula 17 and a stylet 19. Cannula 17, which is preferably a unitary structure made of molded plastic, includes a tubular member 21 and an annular flange 23. Tubular member 21, which has a longitudinal bore 22, is shaped to include a generally cylindrical distal portion 25, a generally cylindrical proximal portion 27, and a generally conical intermediate portion 29. Distal portion 25 and proximal portion 27 are comparatively sized so that distal portion 25 has a smaller inner diameter and a smaller outer diameter than does proximal portion 27. Intermediate portion 29 is appropriately sized so that its inner and outer diameters taper from proximal portion 27 to distal portion 25. As explained further below, because of its interior shape, cannula 17 limits insertion of stylet 19 into a patient.

Annular flange 23 radially surrounds the exterior of tubular member 21 in the area between proximal portion 27 and intermediate portion 29. As will be apparent from the description below, distal portion 25 is adapted to pass through the abdominal and stomach walls of a patient, with annular flange 23 remaining outside the patient's body and acting as a stop to limit insertion of cannula 17 into the patient.

Stylet 19, which is adapted for removable insertion into cannula 17, is a unitary structure made, for example, of a rigid metal, such as stainless steel. Stylet 19 is shaped to include a proximal base 41 and a distal stem 43, distal stem 43 terminating in a sharp tip 45. Base 41 and stem 43 are appropriately dimensioned so that, when stylet 19 is fully inserted into bore 22 of cannula 17, base 41 abuts the inner surface of intermediate portion 29 to prevent further insertion of stylet 19 though cannula 17, with tip 45 extending distally beyond distal portion 25.

It should be understood that, access needle 13 need not have the structure described above and may be, for example, a conventional access needle.

Figure 2:
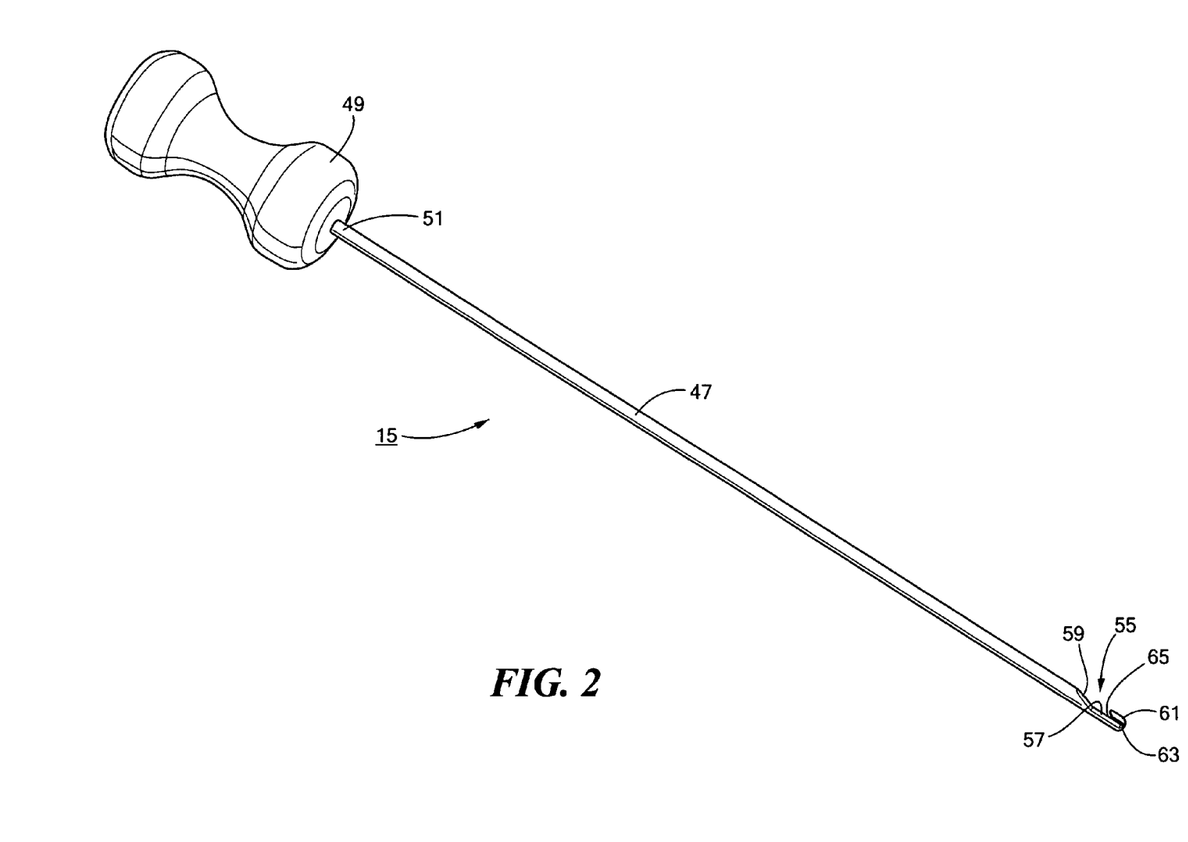
FIG. 2 is an enlarged, perspective view of the guide element grasping tool shown in FIG. 1.
Figure 3:
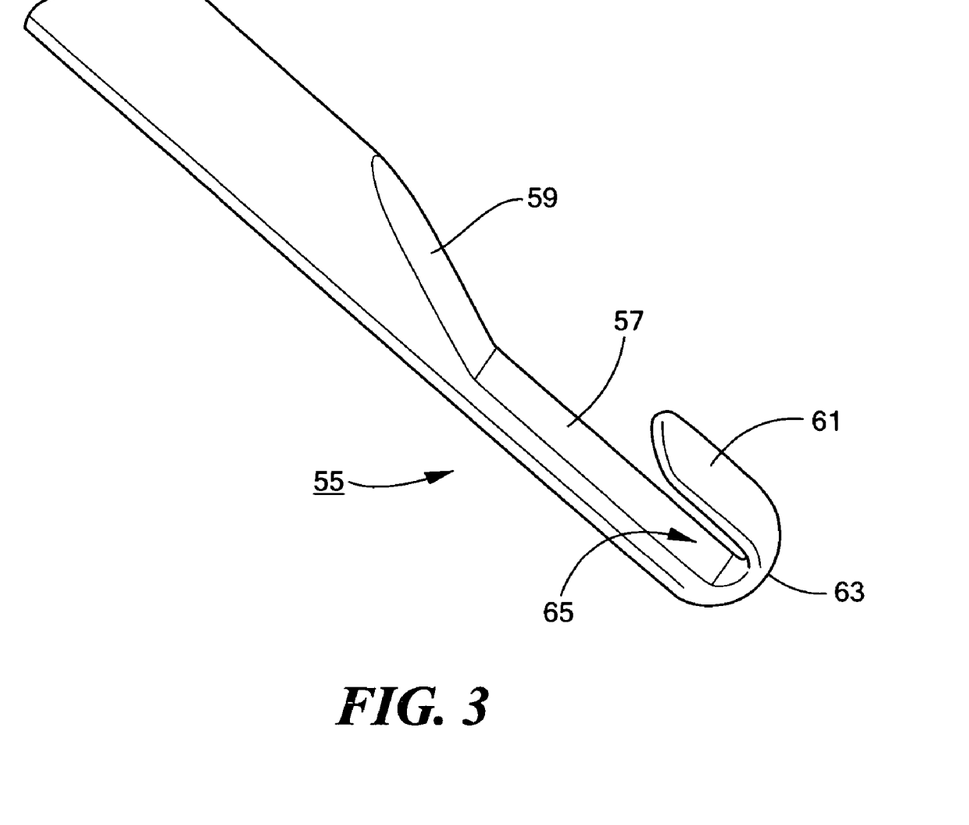
FIG. 3 is an enlarged, fragmentary, perspective view of the distal end of the guide element grasping tool shown in FIG. 2.

Guide element grasping tool 15, which is also shown separately in FIGS. 2 and 3, includes an elongated rigid shaft 47. A handle 49 is fixedly mounted on a proximal end 51 of shaft 47. A distal end of shaft 47 is shaped to define a J-hook 55 terminating in a rounded distal tip. Specifically, J-hook 55 includes a thin, flat surface 57 which extends distally from a beveled surface 59 that is provided in shaft 47. A short finger 61 is connected to the distal end of surface 57 by a bend 63, finger 61 extending substantially parallel to surface 57 to define a shallow slot 65. As will be described below, slot 65 is adapted to receive a portion of a guide element, such as a length of a pushwire or a loop of a puliwire.

Referring now to FIGS. 4(a) through 4(h), there is shown the manner in which kit 11 may be used to position a guide element, such as a pushwire or a pullwire, in a patient for subsequent PEG device implantation. First, an endoscope E is inserted transorally into the stomach of the patient, and an intense light source L disposed within endoscope E is used to transilluminate the stomach wall S and the abdominal wall A of the patient so as to indicate externally a desired incision site (see FIG. 4(a)). Preferably, while the aforementioned transillumination process is conducted, a supply of gas is used to inflate the patient's stomach, thereby distending the stomach and facilitating the transillumination process. Next, a scalpel incision is made at the desired incision site, and access needle 13 is inserted into the incision, with the proximal end of access needle 13 remaining external to the patient and the distal end of access needle 13 extending into the patient's stomach (see FIG. 4(b)). Stylet 19 is then removed from the patient while keeping cannula 17 in place (see FIG. 4(c)).

Figure 4A:
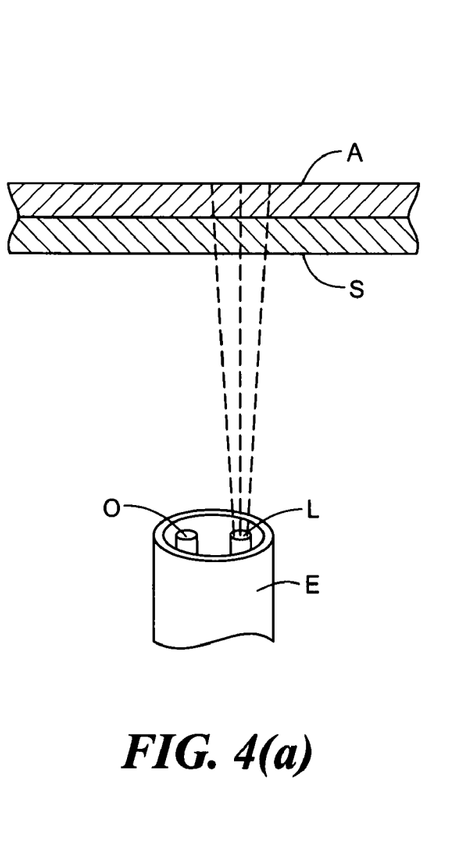
FIG. 4(a) through 4(h) are fragmentary, schematic views, partly in section, illustrating the manner in which the kit of FIG. 1 may be used to position a guide element in a patient in accordance with the present method.
Figure 4B:
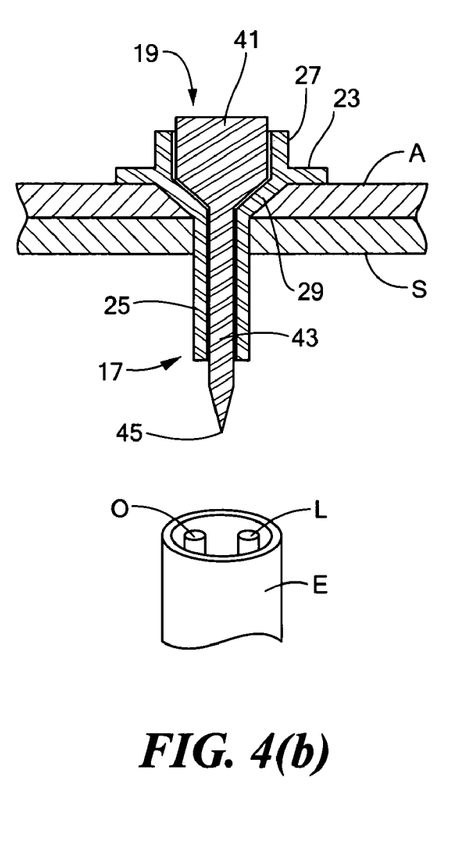
Figure 4C:
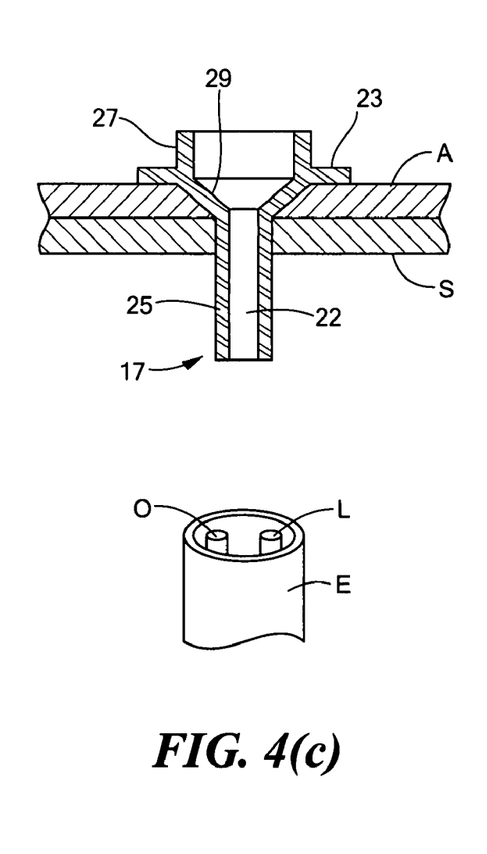
Figure 4D:
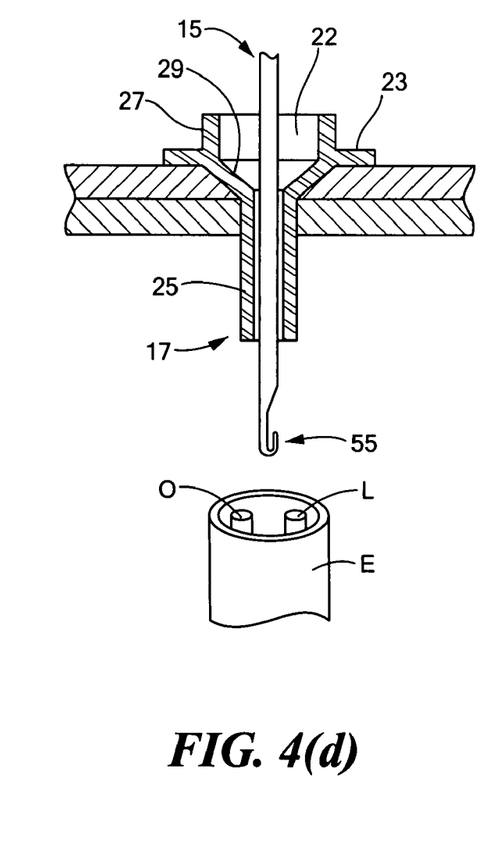
Figure 4E:
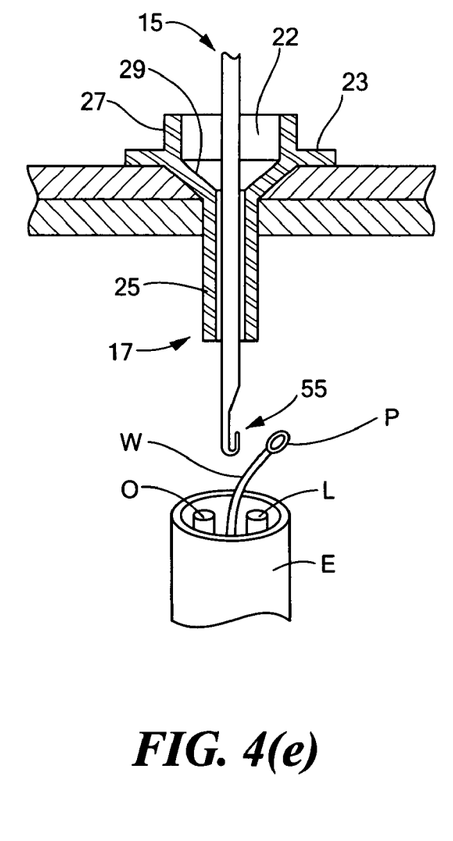
Figure 4F:
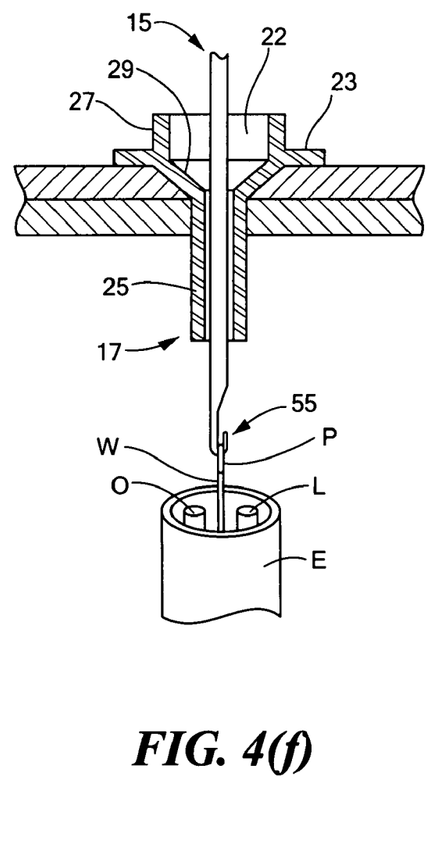
Figure 4G:
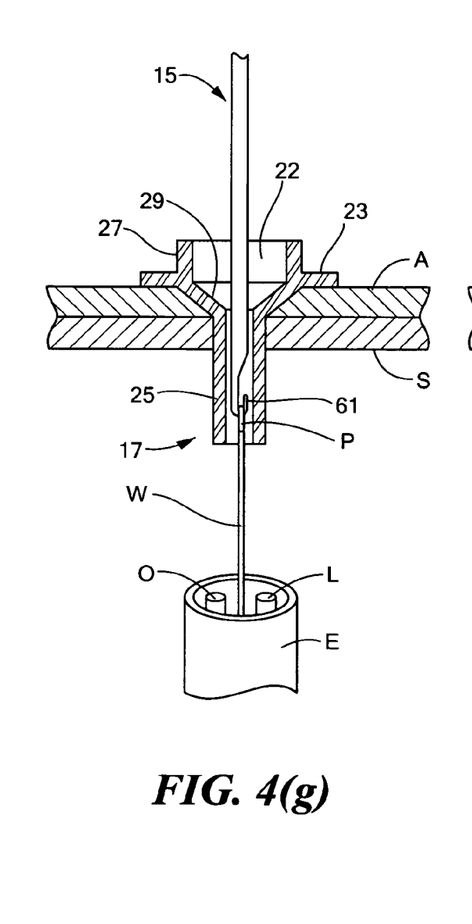
Figure 4H:
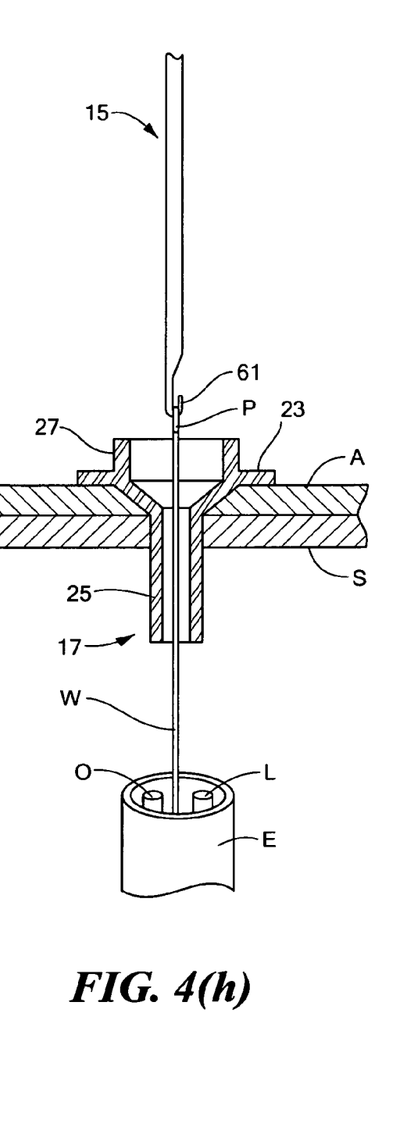
Figure 5A:
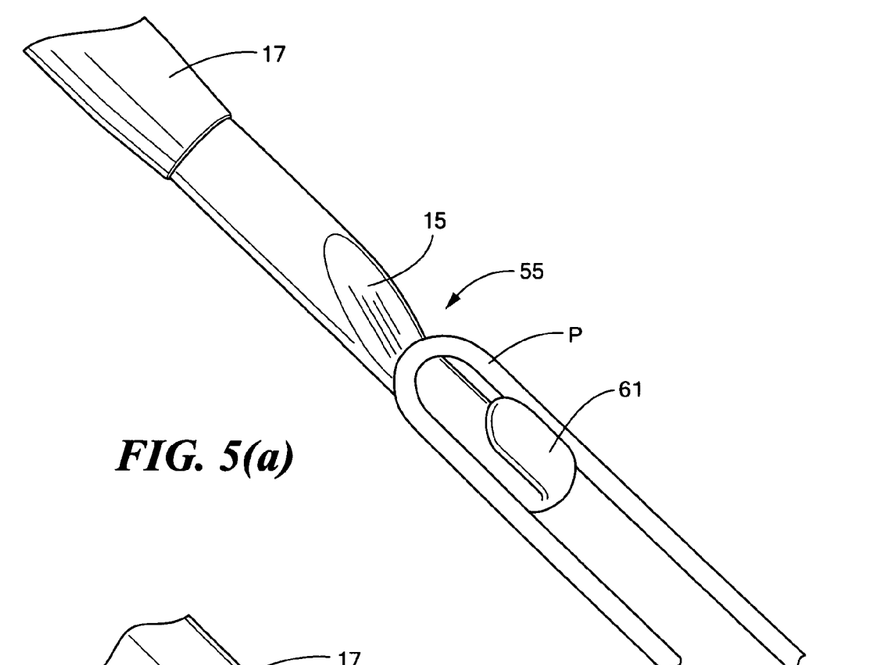
FIGS. 5(a) and 5(b) are enlarged, fragmentary, perspective views, illustrating in greater detail certain aspects of FIGS. 4(f) and 4(g), respectively.
Figure 5B:
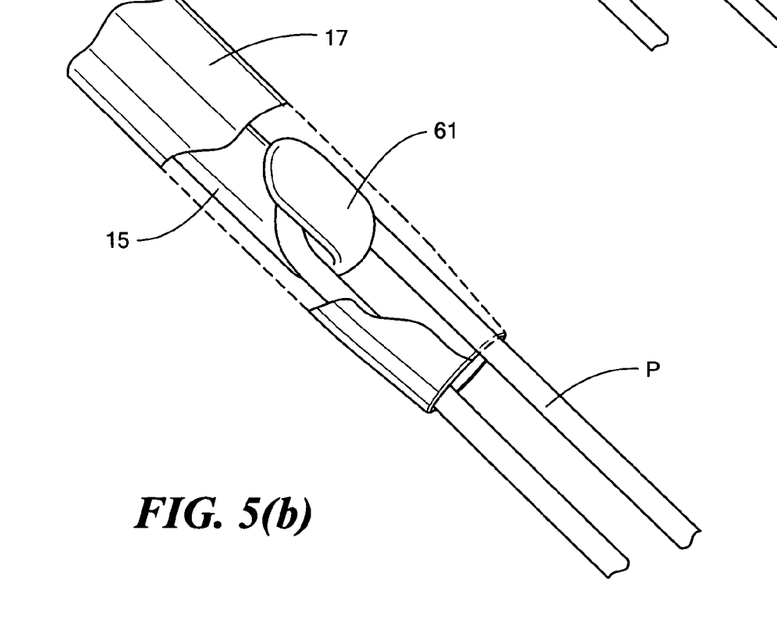

Next, while observing the distal end of cannula 17 using observation optics O disposed within endoscope E, the distal end of guide element grasping tool 15 is inserted through cannula 17 and into the patient's stomach (see FIG. 4(d)). The leading end of a guide element, in this case a looped leading end P of a pullwire W, is then inserted distally through endoscope E, where it is positioned in the vicinity of J-hook 55 (see FIG. 4(e)). Tool 15 is then manipulated until J-hook 55 catches looped leading end P (see FIGS. 4(f) and 5(a)). Next, tool 15 and looped leading end P are withdrawn into cannula 17 (see FIGS. 4(g) and 5(b)) and then removed entirely from the patient (see FIG. 4(h)). Endoscope E is then withdrawn from the patient over the trailing end of pullwire W.

As a result of the above-described procedure, the pullwire is positioned in the patient's body so that the trailing end of the pullwire extends from the patient's mouth and the leading end of the pullwire extends from the abdominal incision. With the pullwire thus positioned in the patient, a PEG device may be implanted in the patient by tying the trailing end of the pullwire to the leading end of a pull-type catheter implanting assembly and then pulling the pullwire through the patient until the gastrostomy feeding tube emerges from the abdomen of the patient and the internal bolster engages the stomach wall of the patient. (If desired, tool 15 may remain hooked to the pullwire and be used to pull the pullwire through the patient.) The implanted device may then be endoscopically checked for proper placement, cut to a desired length, and secured to an external bolster, Y-port and/or clamp in the conventional manner.

As noted above, the above-described method and device are not limited to use with pullwires and PEG devices implanted using "the pull method." Rather, it is to be understood that the above-described method and device may also be used with pushwires and PEG devices implanted using "the push method," as well as with many other types of guide elements and medical catheters. (To use the subject device with a pushwire or similar element lacking a looped end, one simply grabs the pushwire at a point located a short distance from the leading end and then pulls the grabbed pushwire into the cannula. The cannula will cause the pushwire to be bent around the hook in a loop-like fashion.)

The present invention provides a number of significant advantages over conventional methods and devices used to position a guide element in a patient's body. More specifically, as noted above, conventional techniques typically use an endoscopic snare to grab the end of a pushwire or pullwire that has been inserted into a patient through an abdominal incision. Once the guide element is grabbed by the snare, the snare and the guide element are then withdrawn through the mouth of the patient. However, one problem with this approach is that the capture of the guide element by the snare and the subsequent retention of the guide element by the snare during withdrawal of the snare from the patient can be difficult as snares were not designed for such tasks. Consequently, it is not uncommon for some physicians to experience difficulty in catching the guide element with the snare or for the snare to lose its hold on the guide element during withdrawal. In such cases where the guide element is lost during withdrawal, re-intubation of the patient is often necessary. In addition, due in part to their actuation mechanisms and their size, snares can be expensive to manufacture and space-consuming to store. Moreover, due to their somewhat delicate nature, snares are easily damaged prior to use. Furthermore, because they must have a sufficient length to permit their insertion through an endoscope while being manipulated externally, snares can be unwieldy to load into an endoscope.

By contrast, tool 15 and its J-hook 55 are specifically designed to permit facile capture of a guide element and to retain said guide element during withdrawal of tool 15 from a patient. In addition, because tool 15 is passed into a patient's abdomen through an abdominal incision and not through the patient's mouth, tool 15 is a more compact and less complicated device than an endoscopic snare, making tool 15 less expensive to manufacture and easier to use. In addition, because of its rigid construction, tool 15 is less likely to be damaged prior to use. Moreover, because pushwires and pullwires typically have much smaller diameters than snares, smaller diameter endoscopes may be used to perform the present procedure, thereby allowing the procedure to be practiced on a larger population of patients, such as pediatric patients.

It should be noted that numerous modifications could be rendered to kit 11 without departing from the spirit of the present invention. For example, in FIG. 6, there is shown a second embodiment of a kit constructed according to the teachings of the present invention, said kit being represented generally by reference numeral 81.

Figure 6:
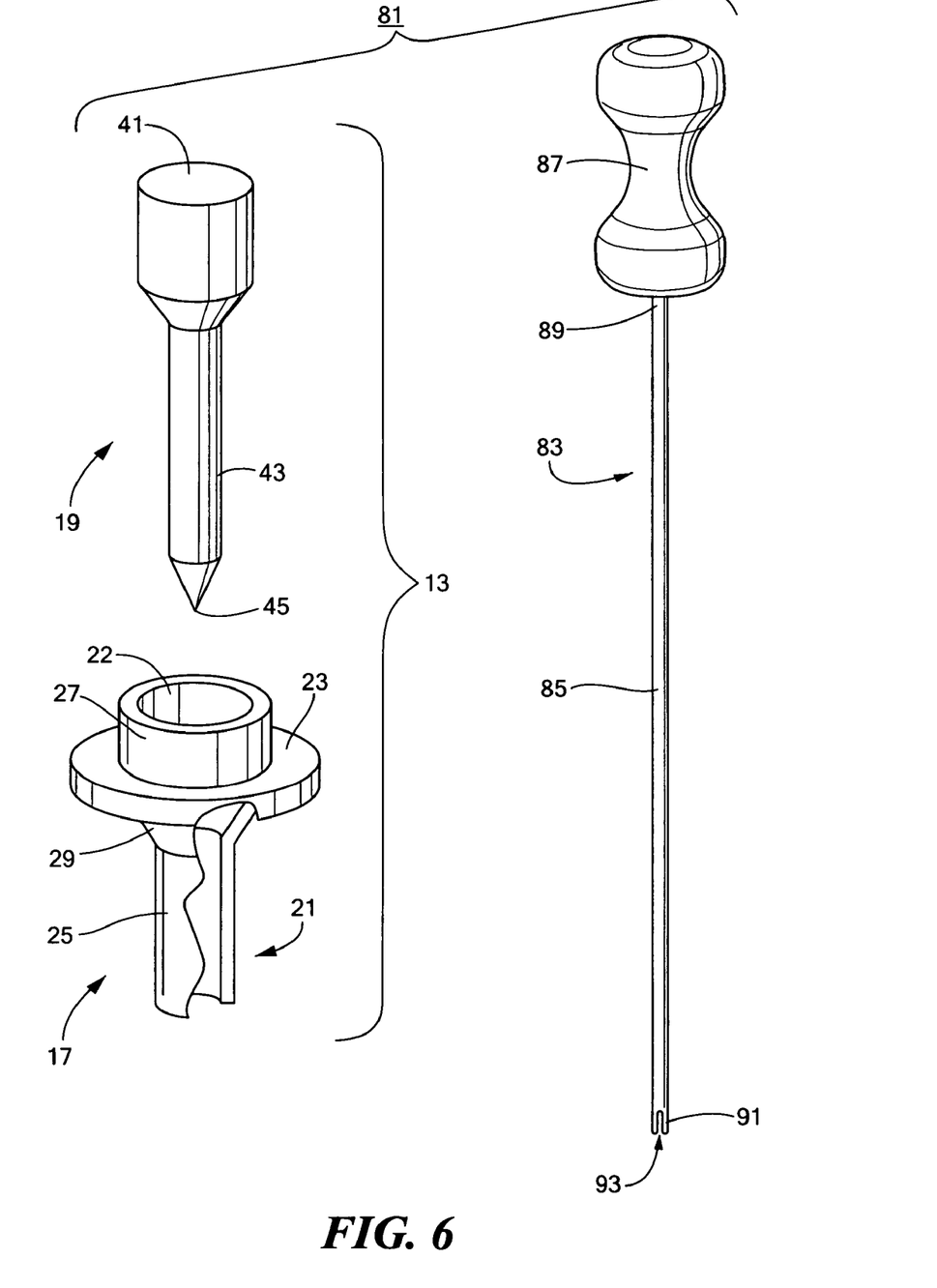
FIG. 6 is an exploded, perspective view of a second embodiment of a kit suitable for use in positioning a guide element in a patient, said kit being constructed according to the teachings of the present invention.

Kit 81 is similar in certain respects to kit 1, the principal difference between the two kits being that kit 81 includes a guide element grasping tool 83, instead of guide element grasping tool 15. Guide element grasping tool 83 includes an elongated rigid shaft 85. A handle 87 is fixedly mounted on a proximal end 89 of shaft 85. A distal end 91 of shaft 85 is bifurcated to define a slot 93. Slot 93 is appropriately dimensioned to securely receive a portion of a guide element, such as a length of a pushwire or a loop of a pullwire.

It should be understood that guide element grasping tool 15 or guide element grasping tool 83 could be modified in other ways to provide alternative guide element grasping structures. For example, the distal end of guide element grasping tool 15 or guide element grasping tool 83 could be in the shape of an arrowhead, could be an apertured structure or could be a barbed structure.

Figure 7:
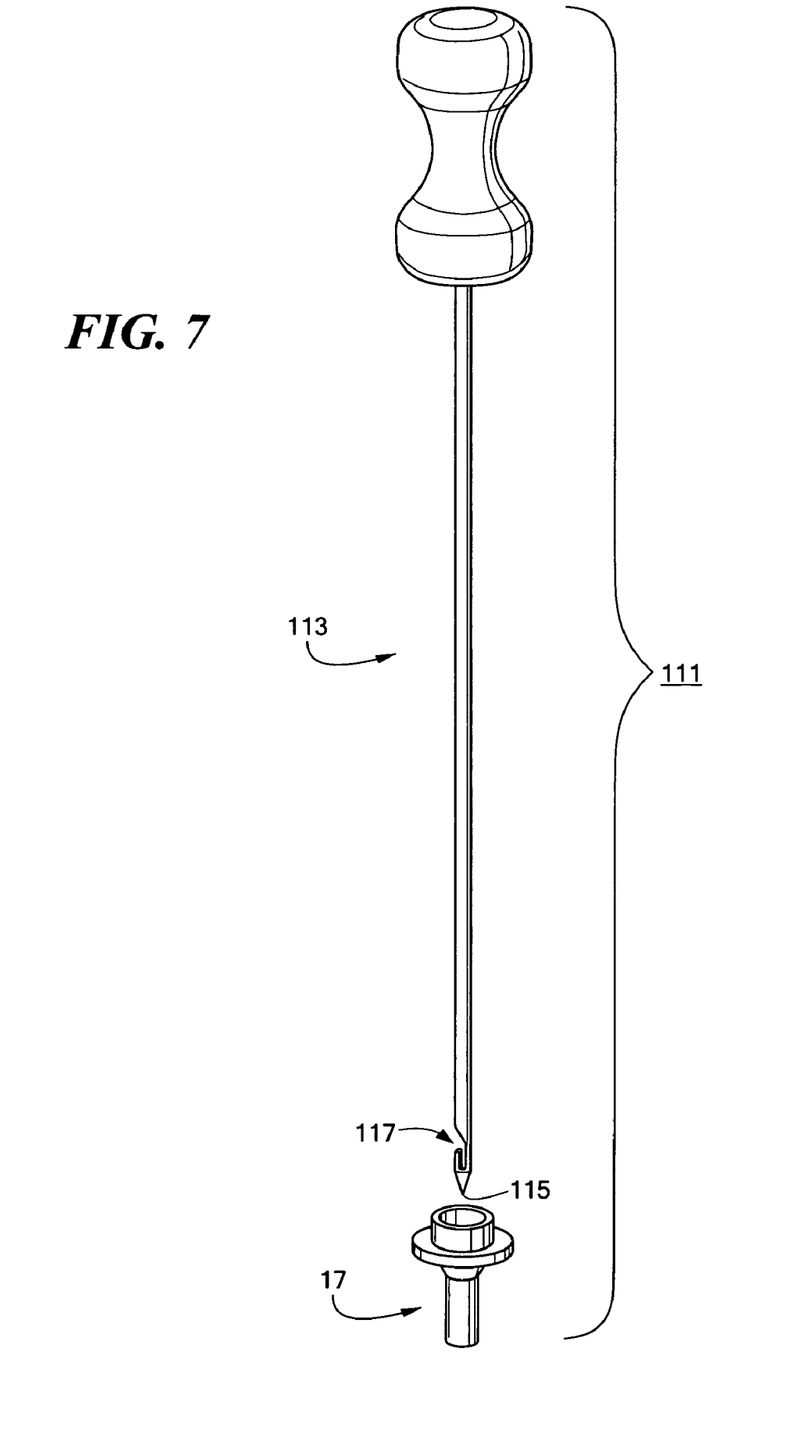
FIG. 7 is an exploded, perspective view of a third embodiment of a kit suitable for use in positioning a guide element in a patient, said kit being constructed according to the teachings of the present invention.

Referring now to FIG. 7, there is shown a third embodiment of a kit constructed according to the teachings of the present invention, said kit being represented generally by reference numeral 111.

Kit 111 is similar in certain respects to kit 11, the principal differences between the two kits being that kit 111 does not include separate stylet and J-hook components, but rather, includes a dual-function tool 113 whose distal end is shaped to include both a needle tip 115 and a J-hook 117. Consequently, tool 113 may be used in the same manner as both stylet 19 of kit 11 and tool 15 of kit 11.

The embodiments of the present invention described above are intended to be merely exemplary and those skilled in the art shall be able to make numerous variations and modifications to it without departing from the spirit of the present invention. All such variations and modifications are intended to be within the scope of the present invention as defined in the appended claims.

What is claimed is:

1. A kit for use in positioning a guide element in a patient, said kit comprising:
   a) a guide element, said guide element being chosen from the group consisting of a guidewire, a pushwire, a suture, or a pullwire, said guide element having a looped distal end and a proximal end adapted to extend out of the mouth of the patient;
   b) an access needle, said access needle comprising a cannula and a stylet, said stylet having a distal end, said stylet being removably receivable in said cannula; and
   c) a guide element grasping tool, said guide element grasping tool comprising a shaft having a proximal end and a distal end, said distal end of said shaft being insertable into the cannula and having means for grasping the looped distal end of the guide element,
   wherein the kit has a first position in which the stylet is received in the cannula and the stylet and the cannula are inserted into a patient's abdominal wall, and a second position in which the guide element grasping tool is inserted through the cannula and the distal end of the guide element grasping tool grasps the looped distal end of the guide element that is positioned inside a patient's body.

2. The kit as claimed in claim 1 wherein said grasping means includes a hook.

3. The kit as claimed in claim 1 wherein said grasping means includes a bifurcated structure.

4. The kit as claimed in claim 1 wherein said grasping means includes a slotted structure.

5. The kit as claimed in claim 1 wherein said shaft is a rigid member.

6. The kit as claimed in claim 1 wherein said guide element grasping tool further comprises a handle mounted on said proximal end of said shaft.

7. The kit as claimed in claim 1 wherein said stylet has a solid stem terminating in a sharp tip.

8. The kit as claimed in claim 1 wherein the cannula includes a tubular member and an annular flange, the annular flange surrounding a portion of the tubular member.

9. The kit as claimed in claim 8 wherein the tubular member is shaped to include a distal portion, a proximal portion, and an intermediate portion.

10. The kit as claimed in claim 9 wherein each of the distal portion and the proximal portion is generally cylindrical in shape,
   wherein the intermediate portion is generally conical in shape,
   wherein the distal portion is smaller in inner diameter and in outer diameter than the proximal portion, and
   wherein the intermediate portion tapers in inner diameter and in outer diameter from the proximal portion to the distal portion.

11. The kit as claimed in claim 10 wherein the annular flange is positioned around a juncture of the proximal portion and the intermediate portion of the tubular member.

12. The kit as claimed in claim 10 wherein the stylet includes a proximal base and a distal stem, the distal stem terminating in a sharp tip, the proximal base and the distal stem being appropriately dimensioned so that, when the stylet is fully inserted into the cannula, the proximal base abuts an inner surface of the intermediate portion of the cannula to prevent further insertion of the stylet though the cannula, with the sharp tip extending distally beyond the distal portion of the cannula.

13. The kit as claimed in claim 1 wherein the cannula is a unitary structure made of molded plastic.

14. The kit as claimed in claim 1 wherein the stylet includes a proximal base and a distal stem, the distal stem terminating in a sharp tip.

15. The kit as claimed in claim 1 wherein the stylet is a unitary structure made of a rigid metal.

16. The kit as claimed in claim 1 wherein the distal end of the shaft of the guide element grasping tool includes a J-hook.

17. The kit as claimed in claim 16 wherein the distal end of the shaft of the guide element grasping tool includes a beveled surface, a flat surface extending distally from the beveled surface, and a short finger connected to the flat surface by a bend, the short finger extending substantially parallel to the flat surface to define a shallow slot.

18. The kit as claimed in claim 1 further comprising an endoscope provided with light means and observation means.

19. The kit as claimed in claim 1 wherein in the second position the stylet is removed from the cannula.

20. The kit as claimed in claim 1, further comprising an endoscope, wherein the guide element extends through a lumen of the endoscope in the first position and in the second position.

21. A kit for use in positioning a guide element in a patient, said kit comprising:
   a) a guide element, said guide element having a looped distal end and a proximal end adapted to extend out of the mouth of the patient;
   b) an access needle, said access needle comprising a cannula and a stylet, said stylet having a distal end insertable through said cannula; and
   c) a guide element grasping tool, said guide element grasping tool comprising a shaft having a proximal end and a distal end, said distal end of said shaft being insertable through said cannula and comprising a rounded J-hook tip;
   wherein the kit has a first position in which the stylet is received in the cannula and the stylet and the cannula are inserted into a patient's abdominal wall, and a second position in which the guide element grasping tool is inserted through the cannula and the distal end of the guide element grasping tool grasps the looped distal end of the guide element that is positioned inside a patient's body, wherein the stylet and the guide element grasping tool are distinct structures.

22. The kit as claimed in claim 21 wherein in the second position the stylet is removed from the cannula.

* * * * *